United States Patent [19]

McEntire et al.

[11] Patent Number: 4,705,898
[45] Date of Patent: Nov. 10, 1987

[54] PREPARATION OF DISECONDARY AMINES FROM DIOLEFINS AND PRIMARY AMINES

[75] Inventors: Edward E. McEntire, Kennett Square, Pa.; John F. Knifton, Austin, Tex.

[73] Assignee: Texaco Inc., White Plains, N.Y.

[21] Appl. No.: 848,173

[22] Filed: Apr. 4, 1986

[51] Int. Cl.$^4$ ............................................. C07C 85/00
[52] U.S. Cl. ................................ 564/467; 564/395; 564/415; 564/448; 564/489
[58] Field of Search ............... 564/467, 489, 415, 395, 564/448

[56] References Cited

U.S. PATENT DOCUMENTS

| | | | |
|---|---|---|---|
| 2,422,632 | 6/1947 | Olin et al. | 528/392 |
| 2,497,310 | 2/1950 | Larson | 260/585 |
| 3,234,283 | 2/1966 | Finch et al. | 260/583 |
| 3,513,200 | 5/1970 | Biale | 260/583 |
| 3,882,181 | 5/1975 | Forster et al. | 260/583 N |
| 3,947,458 | 3/1976 | Iqbal | 260/293.51 |
| 4,005,143 | 1/1977 | Bohm et al. | 260/575 |
| 4,096,150 | 6/1978 | Berthoux et al. | 564/467 X |
| 4,159,996 | 7/1979 | Love et al. | 260/570.5 P |
| 4,179,469 | 12/1979 | Imai | 260/577 |
| 4,197,260 | 4/1980 | Siclari et al. | 260/585 C |
| 4,215,073 | 7/1980 | Cornils et al. | 260/563 D |
| 4,218,399 | 8/1980 | Siclari et al. | 260/583 P |
| 4,292,242 | 9/1981 | Laine | 260/326.8 |
| 4,322,530 | 3/1982 | Jachimowicz | 564/467 X |
| 4,334,042 | 6/1982 | Matsumoto et al. | 564/467 X |
| 4,356,334 | 10/1982 | Imai | 564/467 X |
| 4,429,157 | 1/1984 | Disteldorf et al. | 564/446 |
| 4,448,996 | 5/1984 | Yanagi et al. | 564/467 |
| 4,503,217 | 3/1985 | Alexander et al. | 564/467 X |
| 4,543,411 | 9/1985 | Knifton et al. | 564/467 X |

FOREIGN PATENT DOCUMENTS 2113210 8/1983 Canada ............................... 564/467

OTHER PUBLICATIONS

Jachimowicz, et al. "Scope and Pathway of Catalytic Aminomethylation of Olefins," J. Org. Chem., 47, pp. 445–447 (1982).
Iqbal, Abul, "Catalytic Aminomethylation of . . . Helvetica Chemica Acta, 54, pp. 1440–1445 (1971).

Primary Examiner—Paul F. Shaver
Attorney, Agent, or Firm—Jack H. Park; Kenneth R. Priem

[57] ABSTRACT

A two-step process for the preparation of secondary amines in good yield from olefins, carbon monoxide, hydrogen and primary amines is described. The intermediate imine may be isolated in good yield as well.

18 Claims, No Drawings

PREPARATION OF DISECONDARY AMINES FROM DIOLEFINS AND PRIMARY AMINES

BACKGROUND OF THE INVENTION

1. Field of the Invention

This invention concerns the preparation of secondary amines, and more particularly the preparation of disecondary amines from diolefins, carbon monoxide, hydrogen and primary amines.

2. Description of the Related Art

Diamines are useful intermediate products finding application in the formation of condensation polymers such as polyamides and in the reaction of polyisocyanates to produce polyureas. Various techniques for preparing diamines are known. For example, see U.S. Pat. Nos. 3,882,181; 4,005,143; 4,159,996; 4,197,260; 4,215,073; 4,218,399 and 4,429,157.

It is further known to prepare amines by reacting an olefin with hydrogen, carbon monoxide and a primary or secondary amine. Various techniques embodying this reaction have also been described.

U.S. Pat. No. 2,422,632 suggests that an olefin may be reacted with carbon monoxide and ammonia or an amine having replaceable hydrogen to form an amide or amine.

U.S. Pat. No. 2,497,310 discloses a process for preparing aliphatic amines by reacting carbon monoxide, hydrogen, ammonia or an amine having at least one hydrogen attached to the amino nitrogen, an organic compound containing olefinic unsaturation, and a catalytic quantity of cobalt.

Further work in this field has been focused primarily on the use of different catalyst systems in an effort to obtain better yields and other improvements. U.S. patents disclosing the various catalyst systems are Nos. 3,947,458; 4,096,150; 4,292,242; 4,179,469 and 4,543,411. Also informative as to these and other variations are Iqbal, Helvetica Chemica Acta, Vol. 54, pp. 1440 to 1445 (1971); Laine, et al., J. Org. Chem. 45, 3370 (1980); Jachimowicz, et al., J. Org. Chem. 47, 445 (1982) and U.S. Pat. No. 4,448,996.

U.S. Pat. No. 3,234,283 to Finch, et al. discloses the synthesis of tertiary amines by the reaction of olefins, secondary amines, carbon monoxide and hydrogen in the presence of certain cobalt carbonyl complexes. Finch, et al. teach that the carbonyl complex contains election-donating trivalent phosphorus compounds such as, for example, trialkyl- or triarylphosphines. The mole ratio of the phosphine to the cobalt is instructed to be between 1 and 2.

U.S. Pat. No. 3,513,200 to Biale describes the preparation of tertiary amines by reaction of secondary amines with an ethylenically unsaturated compound, carbon monoxide and hydrogen in the presence of a complex catalyst comprising a Group VIII noble metal hydride in complex with a biphyllic ligand such as an arylphosphine. Biale teaches that the biphyllic ligand may be added directly to the reaction medium, and is preferably used in excess (e.g. 30% to 300%) of that required to form a complex with the Group VIII noble metal, the complex generally comprising 1 to about 5 moles of biphyllic ligand per atom of the metal.

From a study of the art, one learns that to obtain a high yield of product amine from an olefin, carbon monoxide, hydrogen and an amine using prior art catalyst systems, one must prepare a tertiary amine. One may attempt the preparation of a secondary amine by reacting an olefin with hydrogen, carbon monoxide and a primary amine using prior art methods, but the yield is found to be disappointingly low due to the formation of formamide by-product.

Applicants have discovered, however, that it is possible to prepare secondary amines in good yield from olefins, carbon monoxide, hydrogen and primary amines using a two-step process.

SUMMARY OF THE INVENTION

The invention is a two-step process for the preparation of secondary amines from olefins, carbon monoxide, hydrogen and primary amines comprising (1) reacting an olefin, carbon monoxide, hydrogen and a primary amine using an effective amount of a catalyst comprising a ruthenium-containing compound in the presence of a quantity of a trialkylphosphine or triarylphosphine such that the initial mole ratio of trialkylphosphine or triarylphosphine to ruthenium is in excess of 80:1, and (2) hydrogenating the imine product of step (1) to a secondary amine.

DETAILED DESCRIPTION OF THE PREFERRED EMBODIMENTS

In the broadest aspect of this invention secondary amines are prepared from an olefin, synthesis gas (a mixture of carbon monoxide and hydrogen) and a primary amine by reacting these reagents with a ruthenium catalyst, and optionally a rhodium catalyst component, in the presence of a large excess of a trialkyl or triarylphosphine, and then subjecting the imine product to catalytic hydrogenation.

Aminomethylation reactions used in this invention to prepare secondary imines from olefins, synthesis gas ($CO/H_2$) and a primary amine can best be represented by the following general equation sequence:

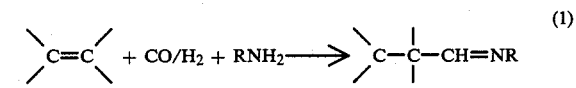

(1)

wherein the reaction occurs in the presence of a large excess of a trialkyl- or triarylphosphine using a ruthenium catalyst, and optionally a rhodium catalyst.

Formation of the secondary amine from the imine product of step (1) then occurs by catalytic hydrogenation as follows:

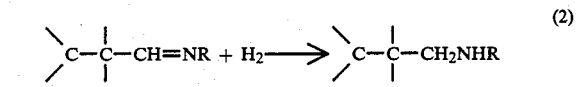

(2)

It is preferred that the trialkyl- or triarylphosphine used in step (1) is present in a quantity such that the initial mole ratio of phosphine to ruthenium catalyst is in excess of 80:1. It is especially preferred that the trialkyl- or triarylphosphine is present in a quantity such that the mole ratio of phosphine to ruthenium catalyst is in excess of 100:1. Most preferred is a trialkyl- or triarylphosphine to ruthenium catalyst mole ratio in excess of 160:1.

The phosphine employed as a catalyst component in the synthesis of the aliphatic imine, equation (1), should contain one or more phosphorus atoms per molecule, and each phosphorus atom should be in the +3 oxidation state, bonded to suitable aryl, alkyl, alkaryl or substituted aryl radicals. In its broadest sense, these phosphines may be trialkylphosphines, triarylphosphines, mixed alkyl-arylphosphines and substituted triarylphosphines, as well as combination thereof. Preferably, the added phosphine is a triarylphosphine. Examples of suitable monodentate triarylphosphines include triphenylphosphine, tri-p-tolylphosphine, tri-p-chlorophenylphosphine, tri-o-tolylphosphine and tri-p-methoxyphenylphosphine. Suitable bidentate or polydentate arylphosphines include 1,2-bis(diphenylphosphino) ethane and 1,5-bis(diphenylphosphino)pentane. The most preferred arylphosphine is triphenylphosphine.

The catalyst employed in step (1) contains a ruthenium-containing component plus, optionally, a rhodium-containing component. The ruthenium-containing compound should be at least partially soluble in the reaction mixture, and should readily convert to the active catalyst in the presence of the carbon monoxide, hydrogen and primary amine co-reactants to allow formation of the desired diimine product. Suitable ruthenium-containing catalyst precursors include ruthenium carbonyls, such as triruthenium dodecacarbonyl, ruthenium oxides such as ruthenium dioxide, hydrate, ruthenium-phosphine complexes such as Iris(triphenylphospine)ruthenium(II) chloride, dichlorodicarbonyl bis(triphenylphosphine)ruthenium(II), and hydrido (acetato)tris(triphenylphosphine)ruthenium(II), as well as ruthenium hydridocarbonyls, suoh as tetrahydridotetraruthenium dodecacarbonyl, and ruthenium acetylacetonates such as ruthenium acetylacetonate.

Suitable optional rhodium-containing catalyst precursors include rhodium carbonyls, such as tetrarhodium dodecacarbonyl, rhodium-phosphine complexes such as hydridocarbonyltris(triphenylphosphine)rhodium(I), chlorotris(triphenylphosphine)rhodium(I), and chlorocarbonylbis(triphenylphosphine)rhodium(I), as well as rhodium oxides such as rhodium-(III) oxide, hydrate, rhodium salts such as rhodium(II) ac oetate dimer and rhodium acetylacetonates such as rhodium (III) acetylacetonate.

Especially preferred ruthenium and rhodium catalyst precursors are, respectively, triruthenium dodecacarbonyl, $Ru_3(CO)_{12}$ and hydridocarbonyltris(triphenylphosphine)rhodium(I), $RhH(CO)(PPh_3)_3$.

The amount of catalyst to be used·may be determined by one of ordinary skill in the art contemplating such factors as the desired reaction selectivity and the economic significance of expensive rhodium and ruthenium.

The calalyst used for the hydrogenation of the diimine to the corresponding diamine in step (2) may be chosen from among those hydrogenation catalysts known in the art. However, though not established by testing, Applicants believe it is preferable that the imine be hydrogenated by a nickel- or cobalt-containing catalyst. This may be a homogeneous or a heterogeneous catalyst and said nickel or cobalt may be bonded to an inert support, or be a significant portion of a bulk metal catalyst, prepared by co-precipitation. The most preferred hydrogenation catalyst for step (2) is believed to be a bulk metal catalyst containing nickel, copper and chromium, prepared by co-precipitation, calcination and reduction. Generally, this bulk metal catalyst should comprise >50% by weight of nickel, and preferably it should contain ca. 70% by weight nickel.

The feedstocks used in the practice of this invention comprise an olefin, a primary amine, carbon monoxide and hydrogen.

The process can be applied to many classes of aliphatic olefins, including aliphatic monosubstituted, disubstituted and trisubstituted olefins containing 2 to 25 carbon atoms, as well as mixtures of the same. Examples of suitable aliphatic olefins include straight-chain terminal olefins such as propylene, 1-butene, 1-octene, 1-decene, 1-dodecene, 1-tetradecene and 1-hexadecene. Also suitable are branched-chain, terminal olefins such as 3-methyl-1-pentene, 4-methyl-1-hexene, 3,3-dimethyl-1-butene and 3,4-dimethyl-1-hexene. Linear and branched, internal olefins are also suitable substrates for this aminomethylation. Examples include 2-octene, 3-octene, 4-octene, mixed internal octenes, mixed internal decenes, mixed internal dodecenes, as well as 2-pentene, 3-hexene, 5-decene, 2-decene, 2-dodecene and 5-methyl-2-hexene.

Cyclic olefins such as cyclohexene, cyclopentene, cycloheptene, and their branched derivatives such as 1-methylcyclohexene and 2-ethylcyclopentene, are particularly useful in the practice of this invention.

Especially preferred in the practice of this invention is the use of non-conjugated diolefins, which result in diimine intermediates and disecondary amines. Suitable diolefin substrates include dicycolo[2.2.1.]hepta-2,5-diene, dicyclopentadiene, 1,9-decadiene, 4-vinyl-1-cyclohexene, 1,2-divinylcyclohexane, 1,19-eicosadiene, 1,5-hexadiene, tricyclopentadiene, 1,4-cyclooctadiene, 1,13-tetradecadiene, 5-vinyl-2-norbornene, 5-vinylbicyclo[2.2.1.]-2-heptene as well as substituted 2,5-norbornadienes. The preferred diolefin is dicyclo[2.2.1.]hepta-2,5-diene, also known as 2,5-norbornadiene.

The primary amines useful in the practice of this invention may be straight or branched-chain aliphalic series, cycloaliphatic amines or aromatic amines. Examples of suitable primary aliphatic and aromatic amines including methylamine, ethylamine, n-propylamine, n-butylamine, ṇ-hexylamine, n-dodecylamine and aniline. Suitable cycloaliphatic amines include cyclohexylamine and cyclopentylamine.

The relative amounts of carbon monoxide and hydrogen which can be initially present in the synthesis gas mixture are variable, and these amounts may vary over a wide range. In general, the mole ratio of $H_2:CO$ is in the range from about 1:10 to about 10:1, and preferably is about 2:1, although ratios outside this range may be employed with good results. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon, and the like, or they may include gases that may or may not undergo reaction under carbon monoxide hydrogenation conditions, such as carbon dioxide, and hydrocarbons, such as methane, ethane, propane and the like.

The reaction is optionally achieved in the presence of a suitable solvent, selected from the classes of organic solvents that include aliphatic amide solvents, aromatic amides, aliphatic and aromatic ether solvents and aromatic hydrocarbon solvents. These solvents should be liquids under the conditions of the aminomethylation reactions.

Suitable amide solvents may be selected from the group of amides that includes N,N-dimethylformamide, N,N-dimethylacetamide, hydroxyethylpyrrolidone, N- methylpyrrolidone, N-isopropylpyrrolidone, N,N-diethylformamide, N,N-dimethylacetamide, N,N-dimethylbenzamide, N,N-diphenylformamide, N,N-dimethylbutyramide and N-benzylpyrrolidone.

Examples of suitable ether solvents include p-dioxane, tetrahydrofuran, tetrahydropyran, diethyl ether, diisopropylether, diphenyl ether, ethylene glycol dimethyl ether, diethylene glycol dimethyl ether and triethylene glycol dimethyl ether as well as mixtures thereof.

Suitable aromatic hydrocarbon solvents include toluene, o-xylene, p-xylene, mixed xylenes, mesitylene, ethylbenzene, benzene, substituted aromatics as well as mixtures thereof.

A preferred class of added solvents for aminomethylation includes N,N-dimethylformamide, N,N-dimethylacetamide, N-substituted pyrrolidones such as N-isopropylpyrrolidone and hydroxyethylpyrrolidone, ethers such as p-dioxane and aromatics such as toluene. An especially preferred solvent is N-methyl pyrrolidinone.

The temperature range which can usefully be employed in the process of the invention may vary over a considerable range depending upon experimental factors, including pressure and other variables. The process can take place at from about 80° C. to about 200° C. The preferred temperatures are above 100° C., and more preferably between 100° C. and 180° C.

Superatmospheric pressures of about 100 psig or greater lead to substantial yields of the desired amines. A preferred range is from about 400 psig to about 4000 psig; although pressures above 4000 psig also provide useful yields of the desired products. A preferred range is from 500 psig to about 2000 psig.

The pressures referred to herein represent the total pressure generated by all the reactants although they are substantially due to the carbon monoxide and hydrogen reactants. The invention will be further illustrated by the following non-limiting examples.

EXAMPLE 1

A glass liner containing 0.92 g (0.01 mole) of bicyclo[2.2.1]hepta-2,5-diene, 8.76 g (0.12 mole) of n-Butylamine, 10.0 g of N-methyl pyrrolidinone and 0.02 g (0.09 mmole Ru) of Ru$_3$(CO)$_{12}$ was charged to a 180 cc rocking 316 stainless steel autoclave. The sealed autoclave was purged with 2:1 H$_2$/CO, then pressured to 500 psig. The contents were heated to 147° C. and pressure was increased to 1100 psig. Pressure decreased in three hours to 975 psig, when pressure was increased to 1000 psig. No further pressure drop was observed after one additional hour. The reactor was cooled and contents discharged. Gas chromatographic-infrared analysis showed that 5.8% of the same was the disecondary amine:

(A)

Three isomers of (A) were present in the sample. About 11% of the sample consisted of a co-product, N-n-butyl acetamide:

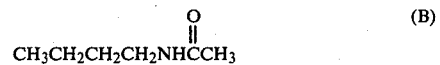

(B)

EXAMPLE 2

In an experiment identical to Example 1, except that 0.095 g (0.45 mmole) of tributylphosphine was also charged to the autoclave, no diamine product was formed.

EXAMPLE 3

In an experiment identical to Example 1, except 4.0 g (15.2 mmole) of triphenylphosphine was added, about 3% of the product solution was diimine (C).

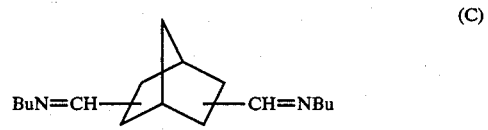

(C)

EXAMPLE 4

To an apparatus as above were charged 10.0 g (108.6 mmole) of bicyclo[2.2.1]hepta-2,5-diene, 18.4 g (70.1 mmole) of triphenylphosphine, 92.0 g NMP, 0.10 g (0.47 mmole Ru) of Ru$_3$(CO)$_{12}$, 0.10g (0.11 mmole Rh) of HRh(CO)(Ph$_3$P)$_3$ and 41 g of methyl amine. The glass liner was omitted. Reaction conditions were 2000 psig, 2:1 H$_2$/CO, 145° C. for six hours. Product observed as about 1.5% of the product mixture was tentatively identified as diimine (D) by gas chromatographic-infrared analysis.

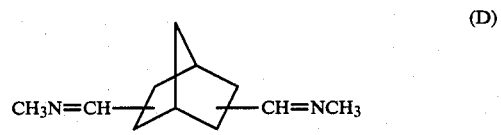

(D)

EXAMPLE 5

Bicyclo[2.2.1]hepta-2,5-diene (84 g, 912 mmole), butylamine (808 g), triphenylphosphine (184 g, 701 mmole), NMP (920 g), Ru$_3$(CO)$_{12}$ (0.92 g, 4.3 mmole Ru), and HRh(CO)(Ph$_3$P)$_3$ (0.92 g, 1.0 mmole Rh) were charged to a one gallon 316 stainless steel autoclave. H$_2$:CO (2:1) was charged at 1000 psig. Reaction conditions were six hours at 145° C., 2000 psig. Distillation of the reaction mixture produced 86 g of a semi-solid b. 148–163° C. (1 mm Hg). Proton nmr confirmed the product was 80+% diimine (C). Spectrum in DCCl$_3$ with Me$_4$Si standard showed a band at 7.6 ppm, characteristic of the imine proton —(HC=N)—].

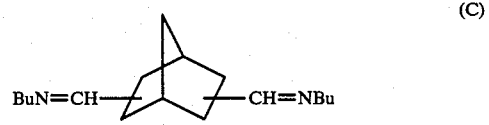

(C)

Infrared analysis showed a sharp band at 1670 cm.$^{-1}$ due to the C=N double bond. Titration with acid showed that the product contained 7.31 meq/g total amine 7.58 theory for (C)].

EXAMPLE 6

Following the procedures of Example 5, the one gallon autoclave was charged with the following materials:

| | |
|---|---|
| Bicyclo(2.2.1)hepta-2,5-diene, g | 84 |
| | 912 mmole |
| Butyl amine, g | 629 |
| Triphenylphosphine, g | 113.0 |
| | 431 mmole |
| N—methylpyrrolidone, g | 920 |
| Triruthenium dodecarbonyl, g | 0.92 |
| | 4.32 mmole Ru |
| HRh(CO)(PPh$_3$)$_3$, g | 0.92 |
| | 1.0 mmole Rh |

After reaction with synthesis gas (CO/H$_2$, 1:1) at 145° C., for six hours at a total pressure of 2000 psig, 1763.2 g of dark, red-dish-green product liquid was recovered. Fractional distillation of the liquid product yielded 14.0 g of a yellow semi-solid (b.p. about 182° C. at 2 mm Hg vacuum) that is shown by nmr and ir to comprise 60% of the diimine product (C).

EXAMPLE 7

Following the procedures of Example 5, the one gallon autoclave was charged with the following materials:

| | |
|---|---|
| Bicyclo(2.2.1)hepta-2,5-diene, g | 84 |
| | 912 mmole |
| Butyl amine, g | 808 |
| Triphenylphosphine, g | 22.6 |
| | 86 mmole |
| N—methylpyrrolidone, g | 920 |
| Triruthenium dodecarbonyl, g | 0.92 |
| | 4.32 mmole Ru |
| HRh(CO)(PPh$_3$)$_3$, g | 0.92 |
| | 1.0 mmole Rh |

After reaction with synthesis gas (CO/H$_2$, 1:1) at 145° C., for six hours at a total pressure of 2000 psig, 1911 g of dark, reddish-green product liquid was recovered. Fractional distillation of the liquid product yielded 29.3 g of a yellow semi-solid (b.p. about 175° C. at 4 mm Hg vacuum) that is shown by nmr and ir to comprise <20% of the imine product (C).

EXAMPLE 8

This example illustrates the conversion of the diimine product (C) to the corresponding desired diamine, A, through a separate catalytic hydrogenation step (eq. 2).

Forty grams of the distilled diimine product, C, from Example 5 was charged to a 300 cc batch reactor along with 150 g of n-butylamine and 3.0 g of a proprietary Ni/Cu/Cr bulk metal catalyst containing about 70% nickel. The reactor was pressured to 1000 psig with hydrogen, heated to 120° C., the pressure raised to 2000 psig with H$_2$, and the autoclave held at temperature for three hours.

Upon cooling, evaporation of the product liquid at 60° C. under vacuum (1 mm Hg) produced 33 g of a liquid product mixture containing (by proton nmr analysis) about 80% of the desired diamine product:

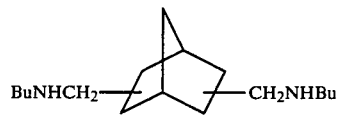

(A)

and 20% of the starting diimine:

(C)

From the preceding examples it may be observed that:

In Example 1, bicyclo[2.2.1]hepta-2,5-diene is aminomethylated in the presence of n-butylamine to give the corresponding disecondary amine derivative, A, in one step using the Ru$_3$(CO)$_{12}$ catalyst precursor alone, with no added phosphine or rhodium catalyst oomponent. The yield of product, A, in this one step procedure is only modest.

In Example 2, using a ruthenium-trialkylphosphine catalyst precursor, no diamine product is formed.

In Example 3, using a ruthenium-triarylphosphine catalyst precursor, the diimine product, (C), is formed in accordance with equation (1).

In Example 4, using a ruthenium-triarylphosphine cataysts precursor, plus an optional rhodium catalyst component, the diimine product is again formed.

In the larger scale experiment of Example 5, using the ruthenium-triarylphosphine-rhodium catalyst combination, the diimine product is prepared and isolated in good yield.

Examples 6 and 7 illustrate the effect of changing the initial phosphine-ruthenium molar ratio on the yield of diimine. Generally, good yields of diimine are achieved when the initial phosphine-ruthenium molar ratio is greater than 80.

The intermediate diimine product, C, is hydrogenated to the corresponding desired diamine, A, in a separate step (eq. 2) in Example 8, using a nickel bulk metal catalyst.

We claim:

1. A process for the preparation of secondary amines from olefins, carbon monoxide, hydrogen and primary amines, comprising
    (a) reacting an olefin, carbon monoxide, hydrogen and a primary amine using an effective amount of a catalyst comprising a ruthenium-containing compound in the presence of a quantity of a trialkylphosphine or triarylphosphine such that the initial mole ratio of trialkylphosphine or triarylphosphine to ruthenium is in excess of 80:1, and
    (b) hydrogenating the imine product of step (a) to a secondary amine.

2. The process of claim 1 in which the quantity of trialkylphosphine or triarylphosphine present is such that the initial mole ratio of trialkylphosphine or triarylphosphine to ruthenium is in excess of 100:1.

3. The process of claim 1 in which the quantity of trialkylphosphine or triarylphosphine present is such that the initial mole ratio of trialkylphosphine or triarylphosphine to ruthenium is in excess of 160:1.

4. The process of claim 1 in which the catalyst employed in step (a) includes a rhodium-containing component.

5. The process of claim 1 in which the triarylphosphine is selected from the group consisting of triphenylphosphine, tri-p-tolylphosphine, tri-p-methoxyphenylphosphine, tri-o-tolylphosphine and tri-p-chlorophenylphosphine.

6. A process for the preparation of disecondary amines from diolefins, carbon monoxide, hydrogen and primary amines, comprising
    (a) reacting a diolefin, carbon monoxide, hydrogen and a primary amine using an effective amount of a catalyst comprising a ruthenium-containing compound in the presence of a quantity of a trialkylphosphine or triarylphosphine such that the initial mole ratio of trialkylphosphine or triarylphosphine to ruthenium is in excess of 80:1, and
    (b) hydrogenating the diimine product of step (a) to a disecondary amine.

7. The process of claim 6 in which the quantity of trialkylphosphine or triarylphosphine present is such that the initial mole ratio of trialkylphosphine or triarylphosphine to ruthenium is in excess of 100:1.

8. The process of claim 6 in which the quantity of trialkylphosphine or triarylphosphine present is such that the initial mole ratio of trialkylphosphine or triarylphosphine to ruthenium is in excess of 160:1.

9. The process of claim 6 in which the catalyst employed in step (a) includes a rhodium-containing component.

10. The process of claim 6 in which the triarylphosphine is selected from the group consisting of triphenylphosphine, tri-p-tolylphosphine, tri-p-methoxyphenylphosphine, tri-o-tolylphosphine and tri-p-chlorophenylphosphine.

11. The process of claim 6 in which the catalyst employed in step (a) includes a rhodium component selected from the group consisting of rhodium carbonyls, rhodium oxides, rhodium-phosphine complexes and rhodium acetylacetonates.

12. The process of claim 6 in which the ruthenium-containing compound of step (a) is selected from the group consisting of ruthenium carbonyls, ruthenium oxides, ruthenium-phosphine complexes and ruthenium acetylacetonates.

13. A process for the preparation of disecondary amines from diolefins, carbon monoxide, hydrogen and primary amines, comprising
    (a) reacting a diolefin carbon monoxide, hydrogen and a primary amine using an effective amount of a catalyst comprising a ruthenium-containing component and a rhodium-containing component in the presence of a quantity of triphenylphosphine such that the initial mole ratio of triphenylphosphine to ruthenium is in excess of 160:1, and
    (b) hydrogenating the diimine product of step (a) to a disecondary amine.

14. The process of claim 13 in which the ruthenium-containing component of step (a) is selected from the group consisting of triruthenium dodecacarbonyl, tris(triphenylphosphine)ruthenium(II) chloride, dichlorodicarbonylbis(triphenylphosphine)ruthenium(II) and ruthenium(III) acetylacetonate.

15. The process of claim 13 in which the rhodium-containing component is selected from the group consisting of tetrarhodium dodecacarbonyl, hydridocarbonyltris(triphenylphosphine)rhodium(I), chlorotris(triphenylphosphine)rhodium(I) and chlorocarbonylbis(triphenylphosphine)rhodium(I).

16. The process of claim 13 in which the diolefin is bicyclo[2.2.1]hepta-2,5-diene.

17. The process of claim 13 in which the diimine product of step (a) is prepared by reacting the diolefin with carbon monoxide, hydrogen and a primary amine in the temperature range of from about 80° C. to about 200° C.

18. The process of claim 13 in which the diimine product of step (a) is prepared by reacting the diolefin with carbon monoxide, hydrogen and a primary amine in the pressure range of from about 400 psig to about 4000 psig.

* * * * *